United States Patent [19]

Harvey et al.

[11] 4,375,460

[45] Mar. 1, 1983

[54] OPAQUE DENTIFRICE

[75] Inventors: Kenneth Harvey, Wilmslow; Harry Hayes, Warrington; Anthony J. Morton, Withington, all of England

[73] Assignee: Colgate-Palmolive, New York, N.Y.

[21] Appl. No.: 304,133

[22] Filed: Sep. 21, 1981

[30] Foreign Application Priority Data

Sep. 24, 1980 [GB] United Kingdom ................. 8030770

[51] Int. Cl.³ .......................... A61K 9/16; A61K 9/18
[52] U.S. Cl. ........................................ 424/52; 424/49
[58] Field of Search ..................... 424/49–58

[56] References Cited

U.S. PATENT DOCUMENTS

| | | | |
|---|---|---|---|
| 2,216,816 | 10/1940 | Kuever | 424/57 |
| 4,130,636 | 12/1978 | Tomlinson | 424/57 |
| 4,152,419 | 5/1979 | Pensak | 424/57 |
| 4,238,476 | 12/1980 | Harvey | 424/57 |
| 4,350,680 | 9/1982 | Harvey et al. | 424/52 |

Primary Examiner—Shep K. Rose
Attorney, Agent, or Firm—Robert L. Stone; Murray M. Grill; Herbert S. Sylvester

[57] ABSTRACT

A dentifrice comprising sodium metaphosphate as a polishing agent and an anionic alkali metal salt of a substantially saturated higher fatty alcohol alkylene oxide sulphate surface active agent is disclosed, the dentifrice having a reduced tendancy to cause sloughing or desquamation.

8 Claims, No Drawings

OPAQUE DENTIFRICE

This invention relates to an opaque dentifrice. In particular, it relates to a dental cream which reduces or avoids the incidence of sloughing or desquamation of oral mucosa.

There are numbers of people who have oral mucosa which are sufficiently sensitive so as to be removed by desquamation or sloughing during the normal toothbrushing regimen, e.g. twice a day for one to two minutes each time. Others may have desquamation occur with more rigorous brushing. This is essentially a cosmetic problem since the mucosa tends to form unsightly residue at the teeth and lips. There is no pain and the mucosa cells are quickly regrown.

Dentifrices such as dental creams and tooth powders typically contain a dentally acceptable water-insoluble dental polishing agent. Insoluble sodium metaphosphate which typically has a water-soluble impurity content of about 2-4% is among the most commonly used dental polishing agents. Likewise, such dentifrices can generally also contain a water-soluble surface active agent, among which sodium lauryl sulphate is very common.

When dentifrices contain both insoluble sodium metaphosphate and an anionic surface active agent such as sodium lauryl sulphate, problems may occur; for instance, sensitive users readily undergo oral sloughing, almost regardless of the pH of the dentifrice (e.g. about 3-7). Since the insoluble sodium metaphosphate is a highly desirable dental component, for example in anti-caries dental creams including a fluorine providing agent such as stannous fluoride or sodium monofluorophosphate, it became desirable to determine whether a surface active agent could be found which has the desirable characteristics of sodium lauryl sulphate but reduces or avoids sloughing of oral mucosa which in contact with insoluble sodium metaphosphate. According to the prevent invention an opaque dentifrice comprising 20-99% by weight of a polishing agent of insoluble sodium metaphosphate and at least 0.2% by weight of an anionic alkali metal salt of a substantially saturated higher fatty alcohol alkylene oxide sulphate containing 12-16 carbon atoms in the alcohol moiety and 1-10 alkylene oxide groups wherein the alkylene groups contain 1-4 carbon atoms. These anionic substantially saturated higher fatty alcohol alkylene oxide sulphate surface active agents have been found to be surprisingly effective in reducing or preventing sloughing, while retaining advantages of anionic surface active agents such as foaming and detersiveness.

The substantially saturated higher fatty alcohol alkylene oxide sulphate surface active agents are used in the form of their alkali metal salts. These surface active agents include those with alcohol moieties having 12 to 16 carbons (12 and 14 being preferred) and from 1 to 10 alkylene oxide groups wherein the alkylene groups contain 1 to 4 carbon atoms, ethylene oxide as a repeating group, 2 to 3 times, being preferred. The preferred compounds of this class are sodium lauryl ether sulphates, such as $C_{12}$-$C_{14}$ alcohol (ethylene oxide) 2-3:1 sodium sulphate. The compounds may be characterised as having the formula $R'O(C_mH_{2m}O)_g OSO_3X$ wherein $R'$ is an alkyl group containing from 12 to 16 carbon atoms, m is from 1 to 4, q is from 1 to 10 and x is an alkali metal. These compounds have been disclosed as additives to clear dentifrices to prevent haze in German published patent application No. 29 18 166. Haze in clear dentifrices of course is not a problem in dentifrices which contain a substantial amount of insoluble sodium metaphosphate, which has a refractive index of 1.51 and is suitable only for use in opaque dentifrices (notwithstanding the disclosures in U.S. Pat. Nos. 2,216,816, and 2,216,821, each issued on Oct. 8, 1940, of translucency of dentifrices containing insoluble sodium metaphosphate, insoluble sodium metaphosphate is generally unsuitable for dentifrices of transparent or translucent character).

British Pat. No. 797,119 discloses alcohol alkylene oxide sulphate as a mild skin detergent but indicates no intraoral use.

It is an advantage of this invention that a substantially non-sloughing dentifrice containing insoluble sodium metaphosphate is provided.

It is a further advantage of this invention that the non-sloughing dentifrice may contain an anti-caries fluorine providing agent such as sodium monofluorophosphate or stannous fluoride.

Additional advantages will be apparent from consideration of the following specification.

As indicated above in the anionic sulphate preferably there are: 12 or 14 carbon atoms in the alcohol moiety; and ethylene oxide as alkylene oxide repeating group of 2-3 e.g. sodium lauryl ether sulphates such as $C_{12}$-$C_{14}$ alcohol (ethylene oxide) 2-3:1 sodium sulphate. 3 repeating ethylene oxide (EO) groups is most preferred. The anionic sulphate is typically employed in the dentifrice in amount of 0.2-5% by weight, preferably 0.5-3% and most preferably 1-2%.

The insoluble sodium metaphosphate used in the dentifrices of the invention is the insoluble sodium salt of polymetaphosphoric acid. It is known in the art as having been often suggested as a dentifrice polishing agent. It may be formed in any suitable manner, for example, as illustrated by Thorpe's Dictionary of Applied Chemistry, Vol. 9 (fourth edition) pages 510-511. The forms of commercially available insoluble sodium metaphosphate known as Madrell's salt and Kurrol's salt are examples of suitable materials. These metaphosphate salts exhibit some solubility in water, but are commonly referred to as insoluble metaphosphates. There is typically present a minor amount of soluble phosphate materials (e.g. sodium tripolyphosphate etc.) as impurities, usually of the order of several percent such as up to about 4% (e.g. 2-4%) by weight, which can contribute to sloughing of oral mucosa when sodium lauryl sulphate is present as surface active agent.

A minor amount (up to about half the total polishing material typically 1-10% by weight of the total) of an additional dentally acceptable polishing agent, particularly a water-insoluble calcium or magnesium salt may be admixed with the insoluble sodium metaphosphate. Such agents include dicalcium orthophosphate dihydrate, anhydrous dicalcium orthophosphate, tricalcium phosphate, calcium pyrophosphate, magnesium orthophosphate, and trimagnesium phosphate. The polishing material comprises 20-99% weight, typically 20-75% by weight of a dental cream and preferably 35-55%, and 75-99% by weight of a tooth powder.

It has also been found that an additional surface active agent may be present and desquamation further reduced, so long as the dentifrice includes at least 0.2% by weight of the anionic higher fatty alcohol alkylene oxide sulphate. The additional surface active agent can even include sodium lauryl sulphate. Such additional agent may be anionic, nonionic, cationic or ampholytic in nature, and it is preferred to employ as the surface-active agent a detersive material which imparts to the dentifrice detersive and foaming properties. Suitable types of such detergents are water-soluble salts of higher (i.e having at least 12 carbon atoms) fatty acid monoglyceride monosulphates, such as the sodium salt of the monosulphated monoglyceride of hydrogenated coconut oil fatty acids, higher alkyl sulphates, such as sodium lauryl sulphate, alkyl aryl sulphonates, such as sodium dodecyl benzene sulphonate, olefin sulphonates, such as sodium olefin sulphonate in which the olefin group contains 12–21 carbon atoms, higher alkyl sulphoacetates, higher fatty acid esters of 1,2-dihydroxy propane sulphonates, and the substantially saturated higher aliphatic acyl amides of lower (i.e. having not more than 4 carbon atoms) aliphatic amino carboxylic acid compounds, such as those having 12–16 carbons in the fatty acid, alkyl or acyl radicals. Examples of the last mentioned amides are N-lauroyl sarcosine, and the sodium, potassium and ethanolamine salts of N-lauroyl, N-myristoyl or N-palmitoyl sarcosine, which should be substantially free from soap or similar higher fatty acid material which tends to substantially reduce the effect of these compounds. The use of these sarcosine compounds in dentifrices is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates of sorbiton monostearate with approximately 60 moles of ethylene oxide condensates of ethylene oxide with propylene oxide condensates of propylene glycol ("Pluronics"—Pluronic is a Trade Mark) and amphoteric agents such as quaternised imidazole derivates which are available under the trade mark "Miranol" such as Miranol C2M. It is noteworthy that nonionic and amphoteric agents assist in reducing sloughing. Quaternised imidazoles such as Miranol C2M are particularly preferred in this regard. Cationic surface active germicides and antibacterial compounds such as disobutylphenoxyethoxyethyl dimethyl benzyl, ammonium choloride, benzyl dimethyl stearyl ammonium chloride, tertiary amines having one fatty alkyl group (of from 12–18 carbon atoms) and two (poly)oxyethylene groups attached to the nitrogen (typically containing a total of from 20 to 50 ethanoxy groups per molecule) and salts thereof with acids, and compounds of the structure,

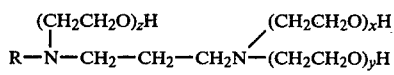

wherein R is a fatty alkyl group typically containing from 12 to 18 carbon atoms, and x, y and z total 3 or higher, as well as salts thereof with mineral or organic acids, may also be used.

In certain forms of this invention a fluorine-providing compound is present in the oral preparation. These compounds may be slightly soluble in water or may be fully water-soluble. They are characterised by their ability to release fluoride ions in water and by substantial freedom from reaction with other compounds of the oral preparation. Among these materials (including mixtures thereof) are inorganic fluoride salts, such as suitable alkali metal, alkaline earth metal, and heavy metal salts, for example, sodium fluoride, potassium fluoride, ammonium fluoride, a copper fluoride, such as cuprous fluoride, zinc fluoride, a tin fluoride such as stannous fluoride, or stannous chlorofluoride, sodium fluorosilicate, ammonium fluorosilicate, sodium fluorozirconate, sodium monofluorophosphate, aluminium mono and di-fluorophosphate, and fluorinated sodium calcium pyrophosphate. Alkali metal and tin fluorides, such as sodium and stannous fluorides and particularly sodium monofluorophosphate are preferred.

The amount of the fluorine-providing compound is dependent to some extent upon the type of compound, its solubility and the type of dentifrice, but it must be a non-toxic amount. It is considered that an amount of such compound which releases a maximum of 1% by weight, based on the weight of the dentifrice is satisfactory. Any suitable minimum amount of such compound may be used, but it is preferable to employ sufficient compound to release from 0.005% to 1%, most preferably about 0.1%, by weight of fluoride ion. Typically, in the cases of alkali metal fluoride and stannous fluoride, this component is present in an amount up to 2% by weight, based on the weight of the dentifrice and preferably in the range of from 0.05% to 1%. In the case of sodium monofluorophosphate the compound may be present in an amount up to 7.6% by weight, more typically 0.76%.

Various other materials may be incorporated in the oral preparations of this invention. Examples are colouring or whitening agents, preservatives, anti-oxidants, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening materials may also be employed. Examples of suitable flavouring constituents are flavouring oils, e.g. oils of spearmint, peppermint, wintergreen, sassafras, clove, sage, eucalyptus, marjoram, cinnamon, lemon and orange, and methysalicylate. Suitable sweetening agents include sucrose, lactose, maltose, sorbitol, sodium cyclamate, perillartine, and saccharin. Suitably, flavour and sweetening agent may together comprise from 0.01% to 5% or more of the preparation.

The dentifrice typically has a pH of 3–8, preferably 3–6. When reference is made to the pH herein, it is intended that the pH determination be made directly on the dentifrice.

The dentifrices are typically prepared by dispersing polishing material in the dental vehicle and adding the oxide sulphate and other components thereto.

The following Examples are further illustrative of the present invention. All amounts are by weight unless otherwise indicated.

EXAMPLES

The following dental creams are prepared:

| | PARTS | | | | | |
|---|---|---|---|---|---|---|
| | A | B | C | D | E | F |
| Sorbitol (70% solution) | 23.00 | 23.00 | 23.00 | 23.00 | 23.00 | 23.00 |
| Viscarin | 1.40 | 1.40 | 1.40 | 1.40 | 1.40 | 1.40 |
| Saccharin acid | 0.14 | 0.14 | 0.14 | 0.14 | 0.14 | 0.14 |
| Insoluble sodium metaphosphate | 45.00 | 45.00 | 45.00 | 45.00 | 45.00 | 45.00 |

-continued

| | PARTS | | | | | |
|---|---|---|---|---|---|---|
| | A | B | C | D | E | F |
| (including 3.53% solubles) | | | | | | |
| Titanium dioxide | 0.40 | 0.40 | 0.40 | 0.40 | 0.40 | 0.40 |
| Ascorbic acid | 0.40 | 0.40 | 0.40 | 0.40 | 0.40 | 0.40 |
| Stannous fluoride | — | 0.62 | — | 0.62 | 0.62 | — |
| Sodium lauryl sulphate | 1.50 | 1.50 | — | 0.75 | 0.38 | — |
| $C_{12}$–$C_{14}$ alcohol EO3:1 Sodium sulphate (28% solution) | — | — | 5.357 | 2.679 | 4.918 | 2.679 |
| Quaternised imidazole (Miranol C2M) | — | — | — | — | — | 0.75 |
| Flavour | 1.00 | 1.00 | 1.00 | 1.00 | 1.00 | 1.00 |
| Water | Q.S. to 100 | Q.S. to 100 | Q.S. to 100 | Q.S. to 100 | Q.S. to 100 | Q.S. to 100. |

Panels rinse teeth with 1:1 dental creams-water slurries of each dental cream A–F once per day on different days. The subjects using dental creams A and B have moderately heavy sloughing of oral mucosa while those using dental creams C–F have only slight sloughing. Retention of soluble tin and fluoride is quite good with dental creams D and E as well as dental cream B.

We claim:

1. An opaque dentifrice comprising 20–99% by weight of a polishing agent of insoluble sodium metaphosphate which tends to cause sloughing of oral mucosa and an effective amount of at least 0.2% by weight of an anionic alkali metal salt of a substantially saturated higher fatty alcohol alkylene oxide sulphate containing 12–16 carbon atoms in the alcohol moiety and 1–10 alkylene oxide groups wherein the alkylene groups contain 1–4 carbon atoms effective in reducing or preventing sloughing, said dentifrice being free from concentrations of sodium lauryl sulphate which cause at least moderately heavy sloughing.

2. A dentifrice as claimed in claim 1 wherein the said sulphate salt has 12–14 carbon atoms in the alcohol moiety, and wherein the alkylene oxide is ethylene oxide and repeats 2–3 times.

3. A dentifrice as claimed in claim 1 wherein the sulphate salt is present in amount of 0.2–5% by weight.

4. A dentifrice as claimed in claim 1 wherein a fluorine-providing compound is present in amount to release up to 1% by weight of fluoride.

5. A dentifrice as claimed in claim 4 wherein up to 2% by weight of stannous fluoride is present.

6. A dentifrice as claimed claim 1 wherein a nonionic or amphoteric surface-active agent is also present which assists in reducing sloughing.

7. A dentifrice as claimed in claim 6 wherein a quaternised imidazole amphoteric surface-active agent is present.

8. A dentifrice as claimed in claim 1 wherein said polishing agent contains about 1–10% by weight of a dentally acceptable water insoluble calcium or magnesium salt polishing agent.

* * * * *